United States Patent
Tessier et al.

(10) Patent No.: US 7,632,802 B2
(45) Date of Patent: Dec. 15, 2009

(54) S100 PROTEIN AS NEUTROPHIL ACTIVATOR FOR ALLEVIATING NEUTROPENIA IN CANCER TREATMENT

(75) Inventors: Philippe Tessier, Montréal (CA); Karen Vandal, Québec (CA); Pascal Rouleau, Québec (CA); Carle Ryckman, Mirabel (CA)

(73) Assignee: Université Laval (CA)

( * ) Notice: Subject to any disclaimer, the term of this patent is extended or adjusted under 35 U.S.C. 154(b) by 227 days.

(21) Appl. No.: 10/551,234

(22) PCT Filed: Mar. 25, 2004

(86) PCT No.: PCT/CA2004/000451

§ 371 (c)(1),
(2), (4) Date: Jul. 11, 2006

(87) PCT Pub. No.: WO2004/084928

PCT Pub. Date: Oct. 7, 2004

(65) Prior Publication Data

US 2006/0281674 A1  Dec. 14, 2006

Related U.S. Application Data

(60) Provisional application No. 60/458,022, filed on Mar. 28, 2003.

(51) Int. Cl.
*A61K 38/00* (2006.01)
*A61K 38/16* (2006.01)
*C07K 14/00* (2006.01)

(52) U.S. Cl. ............... 514/2; 530/350; 530/402; 424/198.1

(58) Field of Classification Search ............... None
See application file for complete search history.

(56) References Cited

U.S. PATENT DOCUMENTS

| | | | |
|---|---|---|---|
| 4,833,074 A | 5/1989 | Fagerhol et al. | |
| 5,350,687 A | 9/1994 | Odink et al. | |
| 5,702,920 A | 12/1997 | Odink et al. | |
| 5,731,166 A | 3/1998 | Geczy et al. | |
| 5,849,528 A | 12/1998 | Hillman et al. | |
| 5,965,122 A | 10/1999 | Namen et al. | |
| 6,015,552 A | 1/2000 | Watanabe et al. | |
| 6,103,497 A | 8/2000 | Hillman et al. | |
| 6,117,989 A | 9/2000 | Bandman et al. | |
| 2003/0003482 A1* | 1/2003 | Halle et al. | 435/6 |
| 2005/0288211 A1 | 12/2005 | Tessier et al. | |

| | | |
|---|---|---|
| 2007/0231317 A1 | 10/2007 | Tessier et al. |

FOREIGN PATENT DOCUMENTS

| | | |
|---|---|---|
| DE | 19811047 | 4/1999 |
| EP | 0219400 | 4/1987 |
| EP | 1066834 | 1/2001 |
| WO | WO 97/34013 | 9/1997 |
| WO | WO 99/47561 | 9/1999 |
| WO | WO 00/20621 | 4/2000 |
| WO | WO 2004/004770 | 1/2004 |

OTHER PUBLICATIONS

Ryckman et al., J. Immunol., Mar. 15, 2003, 170(6):3233-3242.*
Zimmer et al., Brain Res. Bull., 1995, 37(4):417-429.*
Salama et al., Eur., J. Surg., Oncol., 2008, 34(4):357-364.*
Devery et al., J. Immunol., 1994, 152:1888-1897.*
Fidler I. J., Cancer Res., 1985, 45:4714-4726.*
Nicastri et al., Int Conf AIDS. Jul. 7-12, 2002; 14: abstract No. MoPeB3201.*
Aboulafia, Chest, 2000, vol. 117:1128-1145.*
Kumar et al. "Dimeric S100A8 in human neutrophils is diminished after phagocytosis" 2001, Journal of Leukocyte Biology, 70:59-64.
Nisapakultorn et al. "Calprotectin expression in vitro by oral epithelial cells confers resistance to infection by porphyromonas gingivalis" 2001, Infection and Immunity, 69:4242-4247.
Passey et al. "S100A8:emerging functions and regulation" 1999, J. Leukocyte. Biol., 66(4):549-556.
Yang et al. << Proinflammatory properties of the human S100 protein S100A12 >>2001, J. Leukoc Biol. 69:986.
Aguiar-Passeti et al. "Epithelioid cells from foreign-body granuloma selectively express the calcium-binding protein MRP-14, a novel down-regulatory molecule of macrophage activation." 1997, J. Leukoc. Biol. 62:852-858.
Barthe et al. "Identification of "cystic fibrosis protein" as a complex of two calcium-binding proteins present in human cells of myeloid origin." 1991, Biochim. Biophys. Acta. 1096:175-177.

(Continued)

*Primary Examiner*—Gary B Nickol
*Assistant Examiner*—Xiaozhen Xie
(74) *Attorney, Agent, or Firm*—Ogilvy Renault, LLP

(57) ABSTRACT

The present invention relates to a method and composition for inducing lymphocyte proliferation and migration, and for reducing the risks of microbial infections in patients immunosuppressed. The present invention particularly relates to the use of S100 protein, such as MRP, to induce the proliferation, differentiation and release of immune cells from bone marrow. More particularly, S100A8, S100A9, S100A12 and S100A8/A9 are administered to patients with lowered neutrophil blood concentrations.

11 Claims, 5 Drawing Sheets

OTHER PUBLICATIONS

Brandtzaeg et al. "Distribution of a formalin-resistant myelomonocytic antigen (L1) in human tissues. II. Normal and aberrant occurance in various epithelia." 1987, American Journal of Clinical Pathology 87:700-707.

Brandtzaeg et al. "The leucocyte protein L1 (calprotectin): a putative nonspecific defence factor at epithelial surfaces." 1995, Adv. Exp. Muc. Immunol.. 371A:201-205.

Bruggen et al. "The molecular nature of the cystic fibrosis antigen (letter)." 1988, Nature, 331:570.

Buisman et al. "Effect of granulocyte colony-stimulating factor on the course of infection with gram-positive bacteria in mice during granulocytopenia induced by sublethal irradiation or cyclophosphamide." 1996, J. Infect. Dis.,174:417-421.

Cornish et al. "S100 protein CP-10 stimulates myeloid cell chemotaxis without activation." 1996, J. Cell. Physiol. 166:427-437.

Dale et al. "Distribution of a new myelomonocytic antigen (L1) in human peripheral blood leukocytes. Immunofluorescence and immunoperoxidase staining features in comparison with lysozyme and lactoferrin." 1985, American Journal of Clinical Pathology 84:24-34.

Dell'Angelica et al. "Primary structure and binding properties of calgranulin C, a novel S100-like calcium-binding protein from pig granulocytes." 1994, J. Biol. Chem. 269:28929-28936.

Donato, R. "Functional roles of S100 proteins, calcium-binding proteins of the EF-hand type." 1999, Bioch. Biophys. Acta 1450:191-231.

Edgeworth et al. "Identification of p8,14 as a highly abundant heterodimeric calcium binding protein complex of myeloid cells." 1991, J. Biol. Chem. 266:7706-7713.

Frosch et al. "Myeloid-related proteins 8 and 14 are specifically secreted during interaction of phagocytes and activated endothelium and are useful markers for monitoring disease activity in pauciarticular-onset juvenile rheumatoid arthritis." 2000, Arthritis. Rheum, 43:628-637.

Giorgi et al. "Antinociceptive effect of the calcium-binding protein MRP-14 and the role played by neutrophils on the control inflammatory pain." 1998, J. Leukoc. Biol. 64:214-220.

Gottsch et al. "Calgranulin C has filariacidal and filariastatic activity." 1999, Infect Immun. 67:6631-6636.

Guignard et al. "Identification and characterization of a novel human neutrophil protein related to the S100 family." 1995, Biochem. J. 309:395-401.

Harrison et al. "Oxidation regulates the inflammatory properties of the murine S100 protein S100A8." 1999, J. Biol. Chem. 274:8561-8569.

Hashemi et al. "Myeloid-related protein (MRP)-8 from cervico-vaginal secretions activates HIV replication." 2001, AIDS, 15:441-449.

Hattorri et al. "Comparative study of the effects of granulocyte colony-stimulating factor and granulocyte-macrophage colony-stimulating factor on generation and mobilization of neutrophils in cyclophosphamide-treated neutropenic mice." 1996, In Vivo, 10:319-328.

Hitomi et al. "A novel calcium-binding protein in amniotic fluid, CAAF1: Its molecular cloning and tissue distribution." 1996, J. Cell. Sci. 109:805-815.

Hofmann et al. "Rage mediates a novel proinflammatory axis: A central cell surface receptor for S100/calgranulinpolypeptides." 1999, Cell. 97:889-901.

Hunter et al. "High level expression and dimer characterization of the S100 EF-hand proteins, migration inhibitory factor-related proteins 8 and 14." 1998, J. Biol. Chem. 273:12427-12435.

Ilg et al. "Amino acid sequence determination of human S100A12 (P6, calgranulin C, CGRP, CAAF1) by tandem mass spectrometry." 1996, Biochem. Biophys. Res. Commun. 225:146-150.

Ivanov et al. "Enzyme-linked immunosorbent assay for human MRP-8/MRP-14 proteins and their quantitation in plasma of hematological patients." 1996, Immunol. Lett. 49:7-13.

Jinquan et al. "Psoriasin: A novel chemotactic protein." 1996, J. Invest. Dermatol., 107:5-10.

Kocher et al. "Functional chemotactic-factor CP-10 and MRP-14 are abundant in murine abscesses." 1996, Infect. Immun. 64:1342-1350.

Koike et al. "Regulation of myeloid-specific calcium binding protein synthesis by cytosolic protein kinase." 1992, Journal of Biochemistry 112:624-630.

Kojima et al. "Human gingival crevicular fluid contains MRP8 (S100A8) and MRP14 (S100A9), two calcium-binding proteins of the S100 family." 2000, J. Dent. Res., 79:740-747.

Komada et al. "Novel specific chemotactic receptor for S100L protein on guinea pig eosinophils." 1996, Biochem. Biophys. Res. Commun. 220:871-874.

Kunz et al. "Macrophage marker 27E10 on human keratinocytes helps to differentiate discoid lupus eryhematosus and Jessner's lymphocytic infiltration of the skin." 1999, Eur. J. Dermatol. 9:107-110.

Lagasse et al. "Cloning and expression of two human genes encoding calcium-binding proteins that are regulated during myeloid differentiation." 1988, Mol. Cell. Biol. 8:2402-2410.

Lau et al. "A chemotactic S100 peptide enhances scavenger receptor and Mac-1 expression and cholesteryl ester accumulation in murine peritoneal macrophages in vivo." 1995, J. Clin. Invest. 95:1957-1965.

Li et al. "S100β induction of the proinflammatory cytokine interleukin-6 in neurons." 2000, J. Neurochem. 74:143-150.

Lugering et al. "Immunohistochemical distribution and serum levels of the $Ca^{2+}$-binding proteins MRP8, PMRP14 and their heterodimeric form MRP8/14 in Crohn's disease." 1995, Digestion, 56:406-414.

Lugering et al. "Importance of combined treatment with IL-10 and IL-4, but not IL-13, for inhibition of monocyte release of the Ca(2+)-binding protein MRP8/14." 1997, Immunology, 91:130-134.

Lugering et al. "Serum 27E10 antigen: a new potential marker for staging HIV disease." 1995, Clin. Exp. Immunol, 101:249-253.

Madsen, P. et al. "Molecular cloning, occurrence, and expression of a novel partially secreted protein "psoriasin" that is highly up-regulated in psoriatic skin." 1991, J. Invest. Dermatol. 97:701-712.

Marti et al. "Host-parasite interaction in human onchocerciasis: Identification and sequence analysis of a novel human calgranulin." 1996, Biochem. Biophys. Res. Commun, 221:454-458.

Mayer et al. "Recombinant murine granulocyte-macrophage colony-stimulating factor augments neutrophil recovery and enhances resistance to infections in myelosuppressed mice." 1991, J. Infect Dis., 163:584-590.

Metcalf et al. "Proliferative effects of purified granulocyte colony-stimulating factor (G-CSF) on normal mouse hemopoietic cells." 1983, J. Cell. Physiol. 116:198-206.

Metcalf, D. "Cellular Hematopoiesis in the Twentieth Century." 1999, Seminars in Hematology, 36:5-12.

Miranda et al. "Total chemical sythesis and chemotactic activity of human S100A12 (En-Rage)." 2001, FEBS Lett 488:85-90.

Murao et al. "A protein complex expressed during terminal differentiation of monomyelocytic cells is an inhibitor of cell growth." 1990, Cell. Growth. Differ. 1:447-454.

Newton et al. "The human S100 protein MRP-14 is a novel activator of the β2 integrin Mac-1 on neutrophils." 1998, J. Immunol. 160:1427-1435.

Odink et al. "Two calcium-binding proteins in infiltrate macrophages of rheumatoid arthritis." 1987, Nature, 330: 80-82.

Pechkovsky et al. "Calprotectin (MRP8/14 protein complex) realease during mycobacterial infection in vitro and in vivo." 2000, FEMS. Immunol. Med. Microbiol. 29:27-33.

Raftery et al. "Novel intra-and inter-molecular sulfonamide bonds in S100A8 produced by hypochlorite oxidation." 2001, J. Biol. Chem. 276:33393-33401.

Roseth et al. "Correlation between faecal excretion of indium-111-labelled granulocytes and calprotectin, a granulocyte marker protein, in patients with inflammatory bowel disease." 1999, Scand. J. Gastroenterol, 34:50-54.

Matthew Rosinski et al., "Quantitative Dynamics of in Vivo Bone Marrow Neutrophil Production and Egress in Response to Injury and Infection", Annals of Biomedical Engineering, vol. 32, No. 8, Aug. 2004, p. 1108-1119.

* cited by examiner

S100 PROTEIN AS NEUTROPHIL ACTIVATOR FOR ALLEVIATING NEUTROPENIA IN CANCER TREATMENT

CROSS-RELATED APPLICATIONS

This application is a national phase entry under 35 U.S.C. 371 of PCT/CA2004/000451, filed on Mar. 25, 2004 and designating the United States, which in turn claims priority under 35 U.S.C. 119(e) of U.S. Provisional Patent Application 60/458,022, filed on Mar. 28, 2003, the specifications of which are hereby incorporated by reference.

TECHNICAL FIELD

The present invention relates to a method and composition for reducing the risk of infection in a patient with lowered neutrophil count. The method comprises the administration of a composition comprising Myeloid Related Proteins (MRP) to the patient, therefore stimulating proliferation, differentiation and release of neutrophils. The present invention finds particular application in helping cancer patients under chemotherapy to maintain an adequate immune barrier.

BACKGROUND ART

One of the serious side effects of anti-cancerous chemotherapy is the diminution of neutrophils in peripheral blood. Patients are therefore at risk of developing opportunistic infections.

Acute neutropenia (occurring over a few days) often develops when neutrophil use is rapid and production is impaired. Chronic neutropenia (lasting months or years) usually arises from reduced production or excessive splenic sequestration of neutrophils. Neutropenia may be classified as whether it arises secondary to factors extrinsic to marrow myeloid cells or whether an intrinsic defect appears to be present in the myeloid progenitors.

Drugs are one of the most common cause of neutropenia. The incidence of drug-induced neutropenia increases precipitously with age; only 10% of cases occur in children and young adults, and more than 50% occur in adults.

Management of acquired transient neutropenia characteristically associated with malignancies, myelo-suppressive chemotherapy, or immunosuppressive therapy differs whether they are congenital or chronic forms of neutropenia. Infections are the major cause of death in these patients, who must therefore be approached with a high index of suspicion. Early recognition and treatment of infections may be lifesaving. If the acute neutropenia is suspected to be drug-induced, all potentially offending drugs should be stopped immediately.

The role of antibiotic prophylaxis in non-febrile neutropenic patients remains controversial. Also, systemic antifungal prophylaxis is not recommended as a routine component in the management of neutropenic patients.

Using glucocorticoids, androgenic steroids, and vitamins to stimulate bone marrow to produce more neutrophils has not proved successful. Two growth factors (cytokines), granulocyte colony-stimulating factor (G-CSF) and granulocyte-macrophage colony-stimulating factor (GM-CSF), are widely used to prevent fever and infections in patients with severe neutropenia (e.g, after bone marrow transplantation and intensive cancer chemotherapy). However, blood formula regeneration takes approximately two weeks, during which time the patient can still acquire infections. Moreover, the control of neutrophil traffic from bone marrow to blood with G-CSF and GM-CSF to reduce the risk of infections during chemotherapy exhibits adverse effects such as bone pain, abnormalities of liver dysfunctions and pleural and pericardial effusions.

Therefore, there is a need for new therapeutic drugs and a method of treatment that are more active and induce less side-effects thereby reducing the duration of neutropenia and increasing the survival rate of patients undergoing chemotherapy or being in immunosuppressive conditions. Such therapy for neutropenia treatment or prevention should be easy and safe to administer, self-limiting, and require few diagnostic tests to follow the course of treatment. Such therapy should be affordable. Such a therapy would reduce the health care costs. The patient should be able to take the treatment on an ambulatory basis, thereby reducing hospital visits while still enjoying a better quality of life. Such therapy should maintain the productivity of the individual.

SUMMARY OF THE INVENTION

The present invention is directed to a method for modulating at least one immune cell type in a patient, human or animal, suffering from neutropenia or at risk of developing neutropenia. The method comprises the step of administering to said patient at least one S100 protein or derivative thereof in a amount sufficient to induce modulating of the cells. The S100 protein promotes a normal range of neutrophils as a percentage of the total blood cell populating the subject.

The preferred S100 protein is taken from a subfamily member, such as Myeloid Related Proteins (MRP) or derivatives thereof.

The present invention also relates to the use of at least one S00 protein or a derivative thereof, such as MRP for the manufacture of a medicament for reducing the risk of microbial infection in a human or an animal.

The present invention also relates to modulating for example stimulating or activating at least one of differentiation, proliferation or migration of the immune cells.

A further aim of the present invention is to provide a method for stimulating release of immune cells from bone marrow comprising providing Myeloid Related Proteins (MRP) or derivatives thereof to said cells.

The present invention also relates to a method for reducing the risk of microbial infection in a patient comprising administering an effective amount of at least one S100 protein or derivatives thereof such as a MRP, to said patient.

In a further aim of the present invention, there is provided the use of at least one S100 protein or derivatives thereof, such as MRP, in the manufacture of a medicament for modulating at least one immune cell type in a patient, or to reduce the risk of microbial infection in a patient.

Finally, the present invention concerns a pharmaceutical composition for use in reducing the risk of microbial infection in a patient, wherein the composition comprises an effective amount of at least one S100 protein of derivatives thereof, such as MRP, and a pharmaceutically acceptable carrier or diluents.

DESCRIPTION OF THE INVENTION

Figure 1:
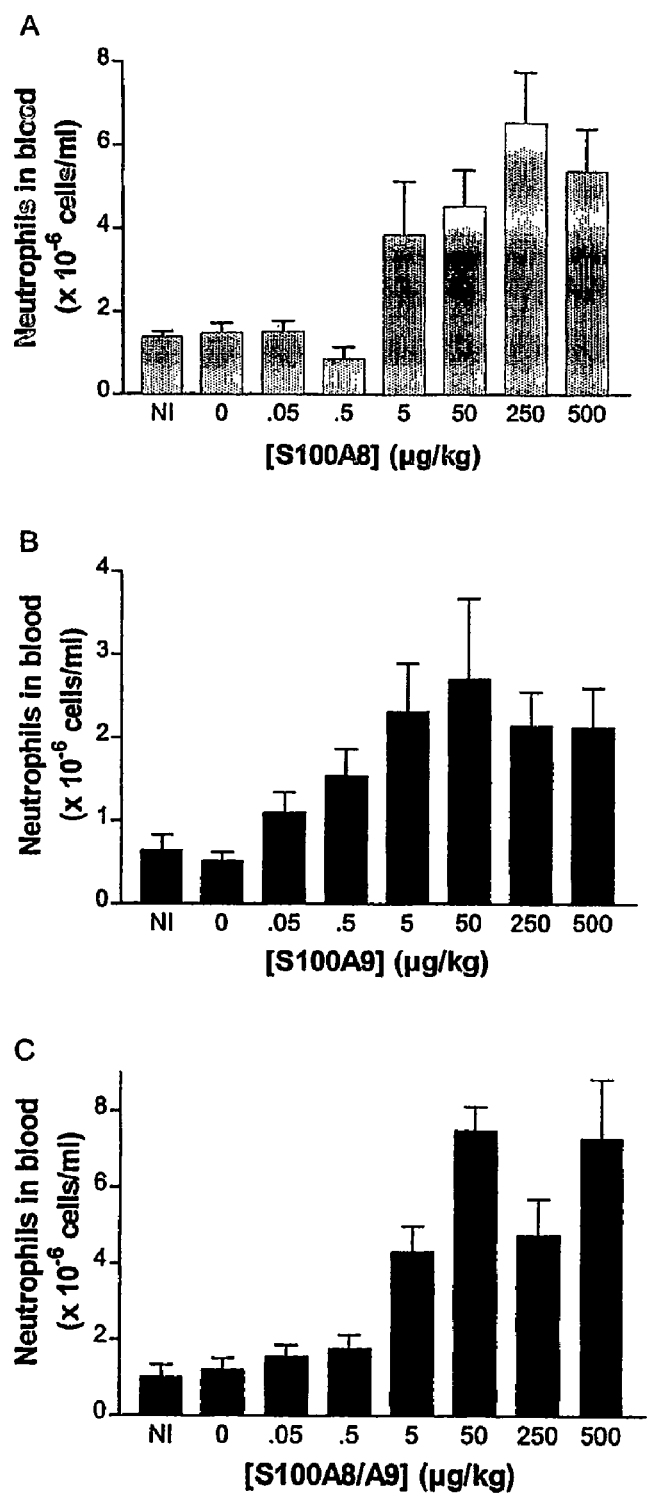
FIGS. 1A to 1C illustrates i.v. injection of S100A8, S100A9, and S100A8/A9 leading to neutrophil accumulation in blood.

The present invention now will be described more fully hereinafter with reference to the accompanying drawings, in which preferred embodiments of the invention are shown. This invention, may, however, be embodied in many different forms and should not be construed as limited to the embodiments set forth herein; rather, these embodiments are provided so that this disclosure will be thorough and complete, and will fully convey the scope of the invention to those skilled in the art.

One first embodiment of the present invention is to provide a method for treating individuals with neutropenia, or at risk of having such disorders. As used herein, "at risk" refers to individuals who have a high probability of acquiring or developing neutropenia, for example, a patient with malignant tumor who is prescribed chemotherapeutic treatment. These treatments frequently lead to a varying degree of myelosuppression. The method comprises of the step of administering to an individual with or at risk of neutropenia, an effective amount of a colony modulating factor, such as a S100 protein or a derivative thereof, such as MRP.

The total number of neutrophils circulating in the peripheral blood of a mouse is estimated at $3 \times 10^6$ cells. Injection of S100A8 (and all other MRPs) in the air pouch led to the migration of more neutrophils than were contained in the blood, suggesting that it induced the release of neutrophils from the bone marrow. This was confirmed by i.v. injections of MRPs which led to the release of neutrophils from the bone marrow to the peripheral blood.

The present invention shows that the myeloid-related proteins (MRP) play a role in the process of neutrophil migration to an inflammatory site. MRP proteins are a subfamily of S100 proteins in which three members of the MRP family have further been characterized, namely S100A8, S100A9 and S100A12, having molecular weight of 10.6, 13.5 and 10.4 kDa respectively, and are expressed abundantly in the cytosol of neutrophils and at lower levels in monocytes. S100A8 and S100A9 are also expressed by activated endothelial cells, certain epithelial cells, keratinocytes and neutrophilic and monocytic-differentiated HL-60 and THP-1. MRPs lack signal peptide sequences so they are not present in granules but rather in the cytosol where they account for up to 40% of the cytosolic proteins. The three MRPs exist as non-covalently-bonded homodimers. In addition, in the presence of calcium, S100A8 and S100A9 associate to form a noncovalent heterodimer called S100A8/A9; these are known as MRP-8/14 complex, calprotectin, p23 and cystic fibrosis antigen as well. S100A8 is also named MRP-8, L1 antigen light chain and calgranulin A and S100A9 is called MRP-14, L1 antigen heavy chain, cystic fibrosis antigen, calgranulin B and BEE22. Other names for S100A12 are p6, CAAF1, CGRP, MRP-6, EN-RAGE and calgranulin C. In this application, the names S100A8, S100A9, S100A12 and S100A8/A9 will be used to designate S100A8 homodimer, S100A9 homodimer, S100A12 homodimer and S100A8/A9 heterodimer, respectively.

Family of the S100 proteins comprises 19 members of small (10 to 14 kDa) acidic calcium-binding proteins. They are characterized by the presence of two EF-hand type calcium-binding motifs, one having two amino acids more than the other. These intracellular proteins are involved in the regulation of protein phosphorylation, enzymatic activities, $Ca^{2+}$ homeostasis, and intermediate filaments polymerisation. S100 proteins generally exist as homodimers, but some can form heterodimers. More than half of the S100 proteins are also found in the extracellular space where they exert cytokine-like activities through specific receptors; one being recently characterized as the receptor for advanced glycation end-products (RAGE). S100A8 and S100A9 belong to a subset of the S100 protein family called Myeloid Related Proteins (MRPs) because their expression is almost completely restricted to neutrophils and monocytes, which are products of the myeloid precursors.

High concentrations of MRP in serum occur in pathologies associated with increased numbers of circulating neutrophils or their activity. Elevated levels of S100A8/A9 (more than 1 μg/ml) are observed in the serum of patients suffering from various infections and inflammatory pathologies such as cystic fibrosis, tuberculosis, and juvenile rheumatoid arthritis. They are also expressed at very high levels in the synovial fluid and plasma of patients suffering from rheumatoid arthritis and gout. High levels of MRPs (up to 13 μg/ml) are also known as being present in the plasma of chronic myeloid leukemia and chronic lymphoid leukemia patients. The presence of these proteins even preceded the appearance of leukemia cells in the blood of relapsing patients. The extracellular presence of S100A8/A9 suggests that the MRPs can be released either actively or during cell necrosis. Like IL-1 and FGFβ, MRPs are expressed in the cytosol, implying that they are secreted via an alternative pathway.

Once released in the extracellular environment, MRPs exert pro-inflammatory functions. These activities are shared by several other S100 proteins. For example, S100 stimulates the release of the pro-inflammatory cytokine IL-6 from neurons and promotes neurite extension. S100L (S100A2) is chemotactic towards eosinophils, while psoriasin (S100A7) is chemotactic for neutrophils and T lymphocytes, but not monocytes.

S100A8, S100A9, and S100A8/A9 are chemotactic for neutrophils, with a maximal activity at $10^{-9}$ to $10^{-10}$ M. Murine S100A8, also called CP-10, is known to be an good potent chemotactic factor for murine myeloid cells with an activity of $10^{-12}$ M. In addition, S100A12 is chemotactic for monocytes and neutrophils and induces the expression of TNFα and IL-1β from a murine macrophage cell line.

MRPs also stimulate leukocyte adhesion to endothelium. S100A9 stimulates neutrophil adhesion to fibrinogen by activating the $\beta_2$ integrin Mac-1. It was recently demonstrated that S100A8, S100A12 and S100A8/A9 also stimulate neutrophil adhesion to fibrinogen. Endothelial cells incubated with S100A12 had increased ICAM-1 and VCAM-1 surface expression, resulting in the adhesion of lymphocytes to endothelial cells. This induction follows activation of NF-κB.

MRPs inhibit oxidative burst either directly or by reacting with oxygen metabolites. S100A9 reduces the levels of $H_2O_2$ released by peritoneal BCG-stimulated macrophages. This effect can be observed using human and murine S100A9, but not S100A8. Unlike S100A9, S100A8 can be efficiently oxidized by $OCl^-$ anions, resulting in the formation of a covalently-linked S100A8 homodimer and loss of its chemotactic activity (demonstrated for murine S100A8). Alternatively, since MRPs are cytosolic proteins, they could protect neutrophils from the harmful effects of its own oxidative burst. S100A9 is also known as being involved in the control of inflammatory pain by its nociceptive effect.

The functions of the MRPs have also been explored in vivo. When injected i.p. into mice, murine S100A8 stimulated the accumulation of neutrophils and macrophages within 4 hours. Inhibition of S100A12 reduced the acute inflammation in murine models of delayed-type hypersensitivity and of chronic inflammation in colitis. All MRPs induce an inflammatory reaction when injected in the murine air pouch model. In this model, sterile air is injected subcutaneously under the dorsum of mice on days 0 and 3. On day 7, an enclosed environment is formed in which it is possible to inject pro-inflammatory products. Injection of S100A8, S100A9, S100A12 or S100A8/A9 in the air pouch led to the accumulation within 3 hrs of up to $8\times10^6$ leukocytes. Leukocytes recruited consisted of neutrophils (80%) and monocytes. The total number of neutrophils circulating in the peripheral blood of a mouse is estimated at $3\times10^6$ cells. Injection of S100A8 (and all other MRPs) in the air pouch led to the migration of more neutrophils than were contained in the blood, suggesting that it induced the release of neutrophils from the bone marrow. This was confirmed by i.v. injections of MRPs which led to the release of neutrophils from the bone marrow to the peripheral blood. These results demonstrate that MRPs are pro-inflammatory and affect leukocyte migration both in vitro and in vivo.

In a preferred embodiment of the present invention, homodimers of S100A8, S100A9 and S100A12, in addition to heterodimers of S100A8/A9 are administered.

Several pro-inflammatory activities have been identified for these proteins. In vitro studies demonstrated that S100A8, S100A9, and S100A8/A9 are involved in neutrophil and monocyte migration and stimulate neutrophil adhesion to fibrinogen by activating the $\beta_2$ integrin Mac-1. In addition, intraperitoneal injection of murine S100A8 in mice stimulates the accumulation of activated neutrophils and macrophages. It is also shown that S100A9 and S100A8/A9 enhance monocyte adhesion to and migration through endothelial cells via Mac-1/ICAM-1 interactions.

In one embodiment of the present invention, there is provided a method for stimulating proliferation, differentiation and releasing from bone marrow of immune cells. This method comprises providing Myeloid Related Proteins (MRP) to the immune cells. Granulocytes such as platelets, basophils, eosinophils, monocytes and macrophages could be stimulated to proliferate and to differentiate in response to increased levels of MRP concentration. Lymphoid stem cell derivatives are also considered as putative target cell for enhancement of immune response by MRPs. Neutrophils are the preferred target when performing the present invention.

In accordance with the present invention, there is provided a method and a pharmaceutical composition for reducing the risk of microbial infection in a patient, which comprise administering an effective amount of S100 protein, such as MRP or derivatives thereof, to the patient. The pharmaceutical composition makes use of S100 protein, such as MRP or their derivatives.

The proteins of the invention may be administered alone or in combination with other types of treatments (e.g., radiation therapy, chemotherapy, hormonal therapy, immunotherapy and anti-tumor agents). Generally, administration of products of a species origin or species reactivity that is the same species as that of the patient is preferred. Thus, in a preferred embodiment, human proteins, fragments derivatives, analogs, or nucleic acids, are administered to a human or animal patient for therapy or prophylaxis. A skilled artisan will however understand that any suitable protein, fragment thereof or polypeptide from any species or genetically altered can be used.

The MRP is employed to stimulate the chemotaxis and activation of macrophages and their precursors, and of neutrophils, basophils, B lymphocytes and some T cell subsets, e.g., activated and CD8+ cytotoxic T cells and natural killer cells, in auto-immune and chronic inflammatory and infective diseases. The etiology of these immune diseases, disorders, and/or conditions may be genetic, somatic, such as cancer or some autoimmune diseases, disorders, and/or conditions, acquired (e.g., by chemotherapy or toxins), or infectious. Moreover, inhibitors or antagonists of S100 polynucleotides or polypeptides can be used as a marker or detector of a particular immune system disease or disorder. MRP can be preferably used for immuno-suppressed patients or patients under chemotherapy for which a lowered count in neutrophils was determined.

The S100 chemokine polynucleotides or polypeptides of the present invention may be employed in combination with a suitable pharmaceutical carrier. Such compositions comprise a therapeutically effective amount of the polypeptide, and a pharmaceutically acceptable carrier or excipient. Such a carrier includes but is not limited to saline, buffered saline, dextrose, water, glycerol, ethanol, and combinations thereof. The formulation should suit the mode of administration. The pharmaceutical composition comprising MRP can be administered subcutaneously, intravenously, intramuscularly, intra-articularly or intraperitoneally. The preferred administration route is the intravenous injection, in order to prevent denaturation of MRP proteins within the gastro-intestinal tract A skilled artisan will understand that non denaturing administration ways are also considered.

Embodiments of the present invention provide a cost-effective therapy for treatment and/or prevention of neutropenia. Individuals are at risk for developing neutropenia or typically exhibit neutropenia in several clinical situations. Individuals may exhibit neutropenia after bacterial or viral infection. Post infectious neutropenia can start within a few days of the onset of the infection and last several weeks. Examples of viral and bacterial agents which give rise to neutropenia comprise varicella, measles, rubella, hepatitis A and B, infectious mononucleosis and influenza, huma-immunodeficiency virus (HIV), brucellosis, tularemia, rickettsia, and M. tuberculosis.

Individuals may exhibit drug induced neutropenia following administering of antineoplastic agents or other drugs which suppress bone marrow. Such drugs include phenothiazines, semisynthetic penicillins, nonsteroidal anti-inflammatory agents, aminopyrine derivatives, and anti-thyroid medication.

Neutropenia may be associated with immunologic abnormalities, (autoimmune neutropenia), metabolic diseases, hypersplenism, and nutritional deficiencies.

The present invention will be more readily understood by referring to the following examples which are given to illustrate the invention rather than to limit its scope.

Example I

S100 Proteins to Induce Neutrophil Proliferation, Differentiation and Release from Bone Marrow i.v. injections of MRPs has been shown to induce the release of neutrophils from the bone marrow. Since S100A8/A9 and S100A12 can inhibit microbial growth, the use of these proteins would have the added benefit of controlling the growth of any microorganism which might have evaded the immune system.

Material and Methods

Recombinant Proteins

Human S100A8, S100A9, and S100A12 cDNAs were synthesized by RT-PCR from neutrophil RNA isolated using Trizol® reagent according to the manufacturer's instructions (GibcoBRL, USA). cDNAs were cloned into the pET28 expression vector (Novagen, Madison, Wis.) and transformed in *E. coli* HMS174. Expression of recombinant MRPs was induced with 1 mM IPTG for 16 h at 16° C. After incubation, cultures were centrifuged at 5,000× g for 10 min. The pellet was resuspended in PBS/NaCl 0.5 M/imidazole 1 mM and lysed by sonication. Lysates were then centrifuged at 55,000× g for 25 min and the supernatants collected. Recombinant His-tag MRPs were purified using a nickel column. His-tag proteins bound to the column were cleaved from their His-tag by adding 10 U of thrombin and incubated for 16 h at room temperature. Recombinant MRPs were eluted with PBS. The digestion and elution process was repeated once to cleave the remaining undigested recombinant proteins. Contaminating thrombin was extracted from the eluates using streptavidin-agarose and contaminating LPS was removed by polymyxin B®-agarose gel (Pierce, Rockford, Ill.). Eluted proteins were analyzed by immunoblot and SDS-PAGE.

Intravenous Injections

Animals were put on a heated cushion to dilate the tail vein 15 minutes before injection. Two hundred μl of S100A8, S100A9, or S100A8/A9 (0.006-60 μg/ml) was then injected i.v. in the tail vein of the mouse, corresponding to 0.05 to 500 μg of protein per kg of body weight. Animals were sacrificed by $CO_2$ asphyxiation at times ranging from 5 min to 24 h later; peripheral blood was collected by cardiac puncture and diluted 1:20 in PBS-EDTA 5 mM. Total leukocytes were counted using a hematocytometer following acetic blue staining. Bone marrow cells were collected by flushing with PBS-EDTA 5 mM through incisions made in the femur, followed by desegregation. Cytospin preparations of both blood and bone marrow cells were analyzed after differential staining with Wright-Giemsa® stain. In some experiments, animals were treated with 150 mg/ml of cyclophosphamide i.p. 24 h prior to being injected with the S100 proteins in order to induce a neutropenia.

Culture of Bone Marrow Cells

Bone marrow cells from CD1 mice were collected by flushing with PBS-EDTA 5 mM through incisions made in the femur, followed by desegregation. Single cell suspensions were cultured in DMEM+10% FCS with methylcellulose added to produce a semi-solid media (StemCell Technologies, Vancouver, BC). Colony formation was stimulated with GM-CSF (200 pg/ml, positive control), and in the presence or absence of 40 μg/ml of S100A8, S100A9, S100A12 or S100A8/A9. Colonies were counted after 7 days of culture (Metcalf et al., 1983, J. Cell Physiol. 116:198; Metcalf et al., 1999, Semin. Hematol. 36:5).

Results

Intravenous Injection in Mice with Neutrophilia

Figure 2:
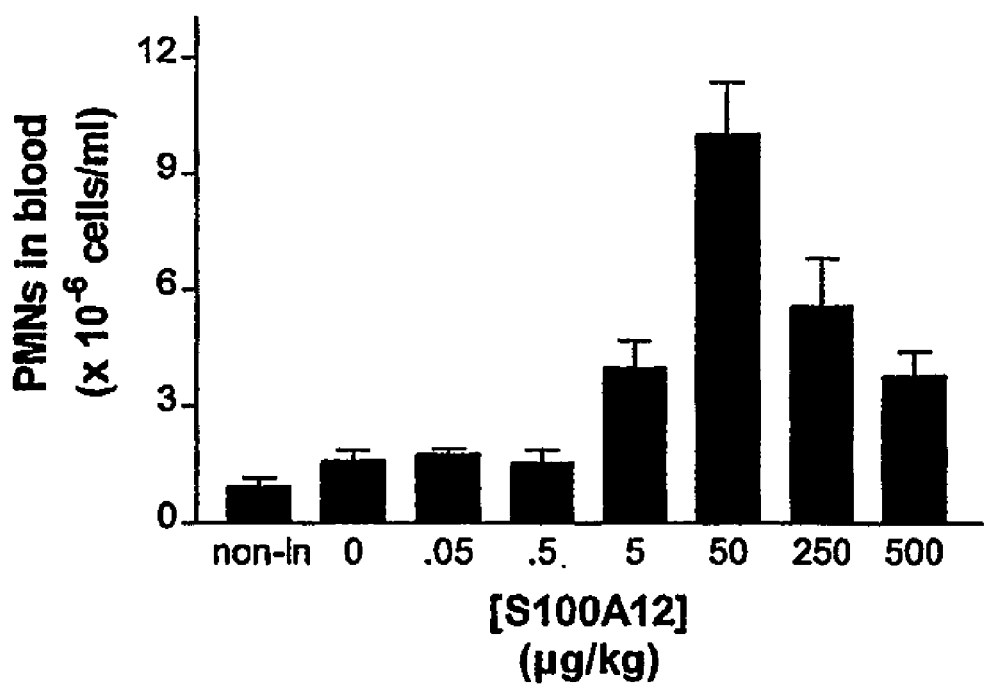
FIG. 2 illustrates i.v. injection of S100A12 leading to neutrophil accumulation in blood.

Increasing doses of S100A8, S100A9, S100A12, and S100A8/A9 were injected i.v. in mice and the peripheral blood was collected 3 hours later. Injection of either S100 protein had no noticeable effects on morbidity such as ruffling of the fur or hunched posture. As shown in FIGS. 1A, B and C, i.v. injection of S100A8, S100A9, and S100A8/A9 caused an increase in the number of circulating neutrophils. The number of neutrophils after injection reached 6.5, 2.7 and $7.4\times10^6$ cells/ml in S100A8, S100A9, and S100A8/A9 injected mice respectively, compared to less than $1.5\times10^6$ cells/ml for the control animals. This increase, detected for injected doses ranging from 5 to 500 μg/kg (0.12 to 12 μg/mice), was significantly different from control ($p<0.05$, two-tailed student-t test) and maximum at a dose of 50 to 250 μg/kg. Although the total number of circulating leukocytes increased slightly in S100 protein-injected mice, this increase was not significantly different from that in PBS-injected mice. Injection of S100A8, S100A9, and S100A8/A9 did not increase the number of circulating eosinophils, monocytes, or lymphocytes (data not shown). Assuming a total blood content of 79 ml/kg, these doses corresponded to serum concentrations ranging approximately from 600 to 3000 ng/ml at the time of injection. Similar results were obtained following injection of S100A12 (FIG. 2).

The kinetic study of S100A8 and S100A9 injection over a 24 h period (FIGS. 3A and 3B) showed that they induced neutrophilia over a period of 3 to 6 h post injection. At 3 h, the number of neutrophils was $2.8\times10^6\pm0.5\times10^6$ cells/ml in S100A8-injected mice and $3.5\times10^6\pm0.7\times10^6$ in S100A9-injected mice, compared to $1.0\times10^6\pm0.2\times10^6$ cells/ml for the control mice ($p<0.05$, two-tailed student t test). The increase in circulating neutrophils returned to the control levels by 12 h post-injection. During the same period, the number of total circulating leukocytes increased slightly. This increase, which was not significantly different from the controls, was probably consecutive to the increase in the number of circulating neutrophils. Injection of vehicle alone (PBS) did not alter the number of circulating neutrophils or leukocytes.

Figure 3:
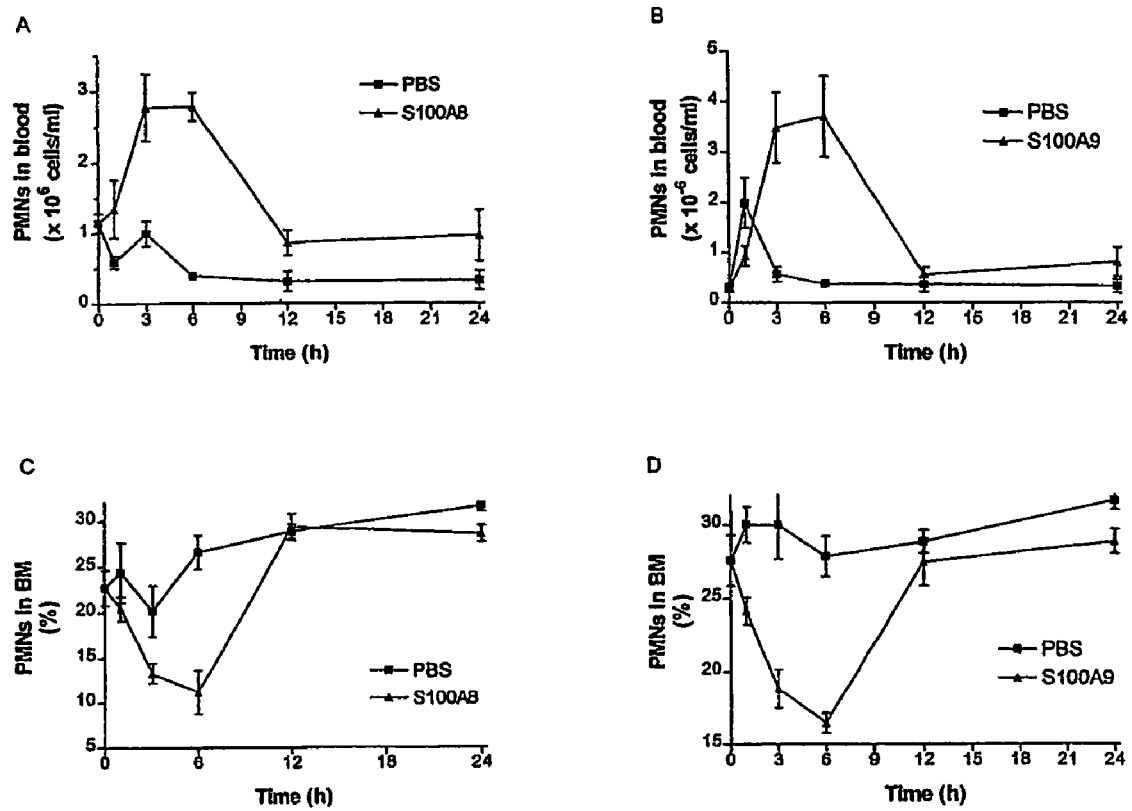
FIGS. 3A to 3D illustrates neutrophils mobilized from the bone marrow to the blood after injection of S100A8 and S100A9.

To determine the origin of the blood neutrophils in S100A8 and S100A9-injected animals, bone marrow differential counts were performed on the same animals (FIGS. 3C and 3D). The increase in the number of neutrophils in the blood induced by S100A8 and S100A9 closely correlated with a decrease in those of the bone marrow. Approximately 22 to 27% of the bone marrow cells in non-injected mice were segmented and non-segmented neutrophils. This percentage did not vary significantly in PBS-injected mice. In contrast, the proportion of neutrophils decreased by 50% in bone marrow cells 3 and 6 h post injection of S100A8 or S100A9 ($p<0.01$ and $p<0.05$, respectively). This strongly suggest that S100A8 and S100A9 induce the release of neutrophils from the bone marrow to the blood.

Induction of Proliferation of Neutrophil Precursors in the Bone Marrow

Figure 4:
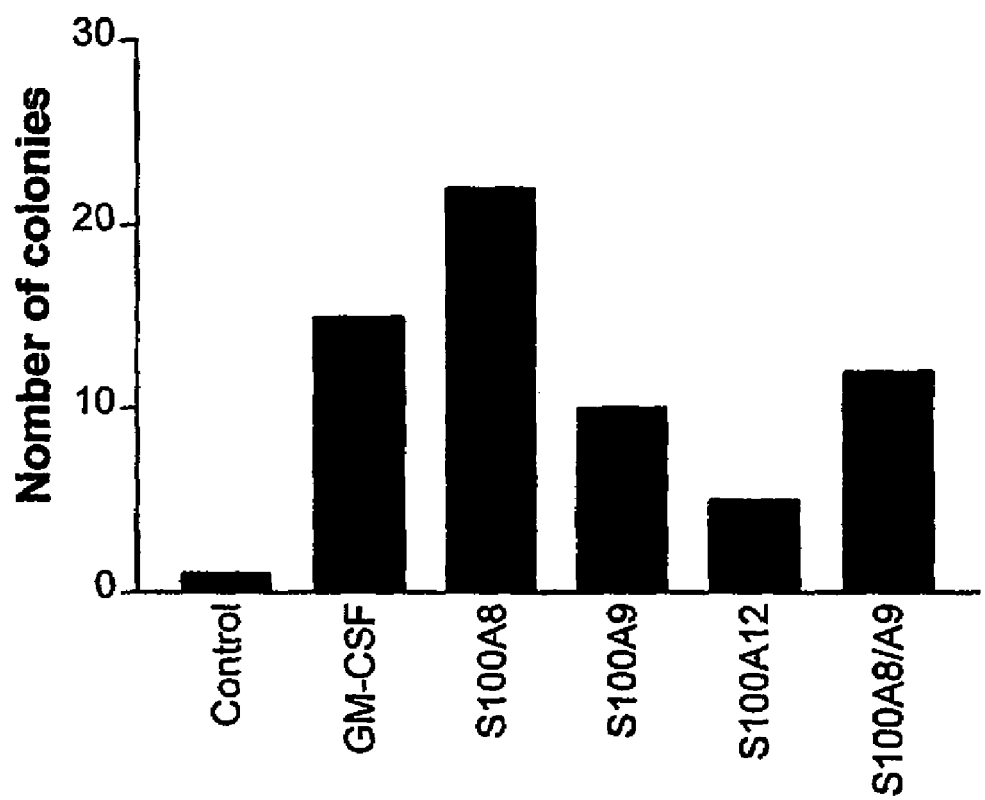
FIG. 4 illustrates S100A8, S100A9, S100A12, and S100A8/A9 inducing the proliferation of neutrophil precursors in the bone marrow.

The colony-stimulating factors act primarily by stimulating the proliferation of early precursors in the bone marrow. To investigate the possibility that S100A8, S100A9, S100A12, and S100A8/A9 stimulate the proliferation of neutrophil precursors, the colony-forming unit assay were used. Single cell suspensions of bone marrow from CD1 mice were cultured in a semi-solid media in the presence of the S100 proteins and the formation of colonies was measured 7 days later. An increase in the number of colonies indicated a proliferative effect of MRPs on early precursors. Few colonies were present in bone marrow cell culture in the absence of growth factors. In contrast, addition of S100A8, S100A9, S100A12, or S100A8/A9 resulted in an increase in the number of granulocyte colonies (FIG. 4). This augmentation was similar to the one observed for bone marrow cells incubated with the growth factor GM-CSF. These results demonstrate that S100 proteins induce the proliferation of neutrophil precursors in the bone marrow.

Treatment of Neutropenia Induced by Anti-Cancerous Chemotherapy Agents in Mice

Figure 5:
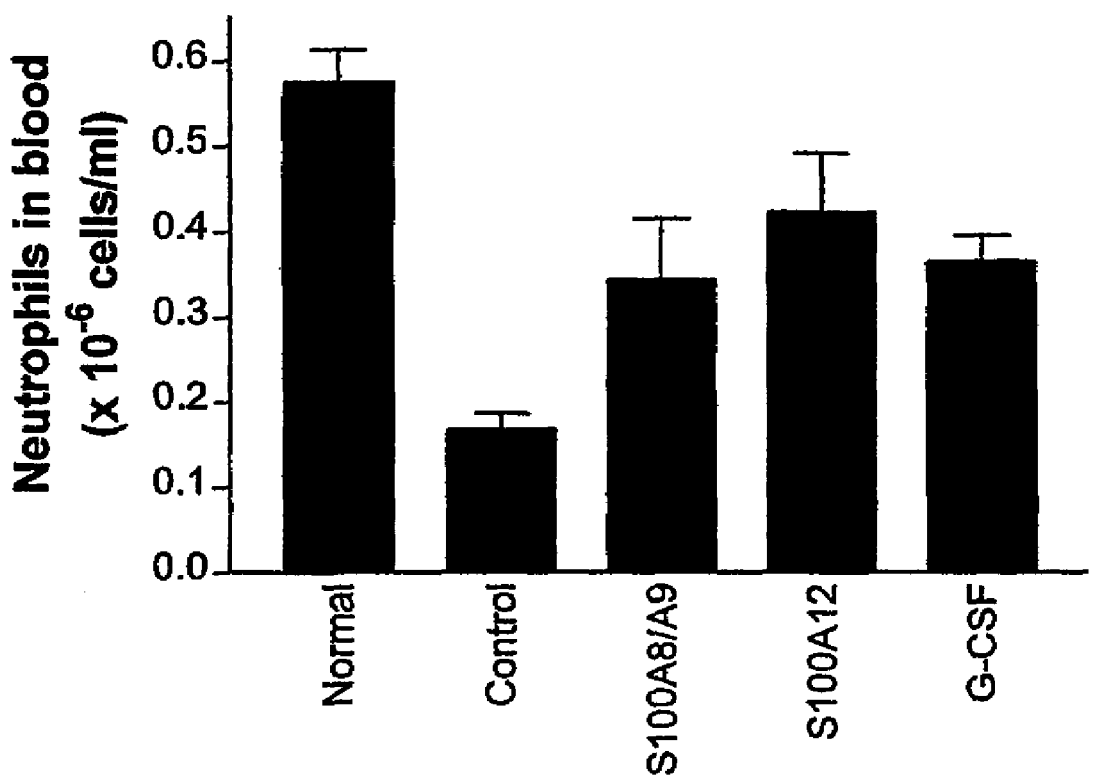
FIG. 5 illustrates IV injection of S100A12 and S100A8/A9 preventing neutropenia induced by anti-cancerous chemotherapy.

It was next determined whether S100A12 and S100A8/A9 could prevent the neutropenia associated with anti-cancerous chemotherapeutic treatment. Mice were injected with the chemotherapy agent cyclophosphamide to induce neutropenia, before being injected daily with 0.5 mg/kg or 1 mg/kg of body weight of S100A8/A9 or S100A12. As shown in FIG. 5, injections of S100 proteins reduced the severity of the neutropenia observed following treatment with cyclophosphamide. This result confirms that S100 proteins can be used to treat neutropenia.

In conclusion, S100A8, S100A9, S100A12, and S100A8/A9 induce the release of neutrophils from the bone marrow to the blood when injected i.v. In addition, they stimulate neutrophil precursor proliferation in the bone marrow. Finally, injection of S100 proteins protect from neutropenia induced by chemotherapeutic agents. These proteins can therefore be used to induce the maturation and release of neutrophils from the bone marrow.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. A method for stimulating or activating differentiation, proliferation and egress of at least one immune cell type in a human patient having neutropenia, the method comprising:
    administering to said patient a therapeutically effective dose of at least one S100 protein selected from the group consisting of: S100A8, S100A9 and S100A12 homodimers, and S100A8/S100A9 heterodimers; and
    measuring the level of circulating mature immune cells in circulating blood of said patient.

2. The method of claim 1, wherein said immune cells are selected from the group consisting of a neutrophil, a monocyte, a macrophage, a platelet, a synoviocyte, a leukocyte and a phagocyte cell.

3. The method of claim 1, wherein said human patient is a patient having neutropenia associated with at least one of: cancer, anti-cancer chemotherapeutic treatment or bone-marrow transplant.

4. The method of claim 1, wherein administering is intravenous, oral, subcutaneous, intramuscular or intraperitoneal administration.

5. A method for treating neutropenia in a human patient suffering therefrom, the method comprising:
    administering to said patient a therapeutically effective dose of at least one S100 protein selected from the group consisting of: S100A8, S100A9 and S100A12 homodimers, and S100A8/S100A9 heterodimers; and
    measuring the level of circulating mature immune cells in circulating blood of said patient.

6. The method of claim 5, wherein said patient has previously been diagnosed to have neutropenia.

7. The method of claim 5, wherein said human patient is a patient having neutropenia associated with at least one of: cancer, anti-cancer chemotherapeutic treatment or bone-marrow transplant.

8. The method of claim 7, wherein said patient has previously been diagnosed to have neutropenia.

9. A method for treating neutropenia in a human patient suffering therefrom, the method comprising:
    administering to said patient a therapeutically effective dose of at least one S100 protein selected from the group consisting of: S100A8, S100A9 and S100A12 homodimers, and S100A8/S100A9 heterodimers; and
    monitoring egress of mature immune cells from bone marrow to peripheral circulation of said patient.

10. The method of claim 9, wherein said human patient is a patient having neutropenia associated with at least one of: cancer, anti-cancer chemotherapeutic treatment or bone-marrow transplant.

11. The method of claim 9, wherein said immune cells are selected from the group consisting of a neutrophil, a monocyte, a macrophage, a platelet, a synoviocyte, a leukocyte and a phagocyte cell.

* * * * *

UNITED STATES PATENT AND TRADEMARK OFFICE
CERTIFICATE OF CORRECTION

PATENT NO. : 7,632,802 B2  Page 1 of 1
APPLICATION NO. : 10/551234
DATED : December 15, 2009
INVENTOR(S) : Tessier et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 454 days.

Signed and Sealed this

Second Day of November, 2010

David J. Kappos
*Director of the United States Patent and Trademark Office*